(12) United States Patent
Tets et al.

(10) Patent No.: US 10,029,990 B2
(45) Date of Patent: Jul. 24, 2018

(54) AGENT FOR INDUCING ENDOGENOUS INTERFERON

(75) Inventors: Viktor Veniaminovich Tets, Saint-Petersburg (RU); Georgy Viktorovich Tets, Saint-Petersburg (RU); Viktor Iosifovich Krutikov, Saint-Petersburg (RU)

(73) Assignees: Viktor Veniaminovich Tets, Saint-Petersburg (RU); Georgy Viktorovich Tets, Saint-Petersburg (RU)

( * ) Notice: Subject to any disclaimer, the term of this patent is extended or adjusted under 35 U.S.C. 154(b) by 0 days.

(21) Appl. No.: 13/883,860

(22) PCT Filed: Oct. 10, 2011

(86) PCT No.: PCT/RU2011/000793
§ 371 (c)(1),
(2), (4) Date: Jun. 5, 2013

(87) PCT Pub. No.: WO2012/064222
PCT Pub. Date: May 18, 2012

(65) Prior Publication Data
US 2013/0261302 A1 Oct. 3, 2013

(30) Foreign Application Priority Data

Nov. 8, 2010 (RU) ................ 2010145438

(51) Int. Cl.
*A61K 31/513* (2006.01)
*C07D 239/22* (2006.01)

(52) U.S. Cl.
CPC .......... *C07D 239/22* (2013.01); *A61K 31/513* (2013.01)

(58) Field of Classification Search
CPC ........................... C07D 239/10; C07D 239/22
USPC .................................... 544/311, 312
See application file for complete search history.

(56) References Cited

U.S. PATENT DOCUMENTS

| 4,314,061 A | 2/1982 | Murdock et al. | |
| 2002/0165240 A1* | 11/2002 | Kimball | A61K 31/435 514/258.1 |
| 2017/0202827 A1 | 7/2017 | Genkin et al. | |
| 2017/0202854 A1 | 7/2017 | Genkin et al. | |

FOREIGN PATENT DOCUMENTS

| JP | 2007314551 A | 12/2007 |
| RU | 2105566 C1 | 2/1998 |
| RU | 2222345 C2 | 1/2004 |
| RU | 2328272 C2 | 7/2008 |
| WO | 9401414 A1 | 1/1994 |
| WO | WO 2000/029389 | 5/2000 |
| WO | WO 0029389 A1 * | 5/2000 ......... C07D 239/545 |
| WO | 2006089221 A2 | 8/2006 |
| WO | 2016/071520 A1 | 5/2016 |

OTHER PUBLICATIONS

Wermuth, Camille. "Molecular Variations Based on Isoteric Replacements." The Practice of Medicinal Chemistry. Academic Press, 1996. pp. 203-237.*
STN Registry File (RN #267649-06-9, entered Jun. 1, 2000).*
Infections: MedlinePlus. (2016) Web: < https://www.nlm.nih.gov/medlineplus/infections.html>.*
New York Times. Health Guide: Tumor. (2014) Web: < http://www.nytimes.com/health/guides/disease/tumor/overview.html>.*
MedicineNet.com (2004) Web: <http://www.medterms.com>.*
Ribatti, Domenico. Leukemia Research 33 (2009) 638-644.*
Sarasin-Filipowicz, Magdalena. PNAS 104(19) (2008) 7034-7039.*
Le, Jennifer. Drug Administration. Merck Manual Consumer Version. (2016) 1-7 Web < http://www.merckmanuals.com/home/drugs/administration-and-kinetics-of-drugs/drug-administration>.*
Alexander, Nancy. Fertility and Sterility. 82 (1) (2004) 1-12.*
Extended European Search Report issued in European Patent Application No. 11839763.7 dated Mar. 11, 2015, 5 pages.
International Preliminary Report on Patentability issued in International Application No. PCT/RU2011/000793 dated Oct. 23, 2012 and English translation of IPRP, 10 pages.
International Search Report issued in International Application No. PCT/RU2011/000793 dated Jan. 19, 2012 and English translation of ISR, 2 pages.
Search performed in priority Application No. RU2010145438, 2 pages, dated Mar. 14, 2011.
Hill, Gale B., "The microbiology of bacterial vaginosis", Am. J. Obstet Gynecol (1993), vol. 169(2) pp. 450-454.
Neovir, RLS (Reestr Lekarstvennih Sredstv Rossii), 2003, p. 572 (http://www.rlsnet.ru/tn_index_id_5706.htm) and English Translation Thereof.
Berkengeim A. M. Khimiya I tekhnologiya sinteticheskikh lekarstvennykh sredvst, 1935, M., Onti Glavnaya redaktsia khimicheskoy literatury, pp. 36-43, especially p. 38 (English Translation).
Communication Pursuant to Article 94(3) EPC Issued in European Patent Application No. 11839763.7, dated Feb. 6, 2017, 5 pages.
Giannini, E. et al., "Validity and Clinical Utility of the Aspartate Aminotransferase-Alanine Aminotransferase Ratio in Assessing Disease Severity and Prognosis in Patients With Hepatitis C Virus-Related Chronic Liver Disease", Archives of Internal Medicine, 2003, 163(2): 218-224.
Kuntsevich, L.D. et al., "Focal immunophysiotherapy in combined treatment of men with manifestations of papilloma virus infection", Urologiia (Moscow, Russia), 2009, 6: 58-62; Abstract.

(Continued)

*Primary Examiner* — Deepak R Rao
*Assistant Examiner* — Laura M Daniel
(74) *Attorney, Agent, or Firm* — Troutman Sanders LLP

(57) ABSTRACT

The invention relates to medicine and can be used for treating a range of diseases in the treatment of which interferon is used. The agent for inducing endogenous interferon is comprised of the compound 6-(3-methoxycarbonyl phenyl) amino-2,4 (1H, 3H)-pyrimidinedione $C_{12}H_{11}N_3O_4$ of general formula: (I). The preparation exhibits greater activity both when injected and when administered orally.

27 Claims, 1 Drawing Sheet

(56) References Cited

OTHER PUBLICATIONS

Schiødt, F. V. et al., "Viral Hepatitis-Related Acute Liver Failure", The American Journal of Gastroenterology, 2003, 98(2): 448-453.
Shibinskaya, M. O. et al., "Synthesis, cytotoxicity, antiviral activity and interferon inducing ability of 6-(2-aminoethyl)-6H-indolo[2,3-b]quinoxalines", European Journal of Medicinal Chemistry, 2010, 45(3):1237-1243.
Shperling, NV. et al., "Treatment of chlamydial infection in chronic prostatitis", Urologiia (Moscow, Russia), 2011, 4:45-47; Abstract.
Tazulakhova, E. B. et al., "Russian Experience in Screening, Analysis, and Clinical Application of Novel Interferon Inducers", Journal of Interferon & Cytokine Research, 2001, 21(2):65-73.
European Communication (Communication pursuant to Article 94(3) EPC) issued by the European Patent Office in European Application No. 11839763.7, dated Jan. 16, 2018.

* cited by examiner

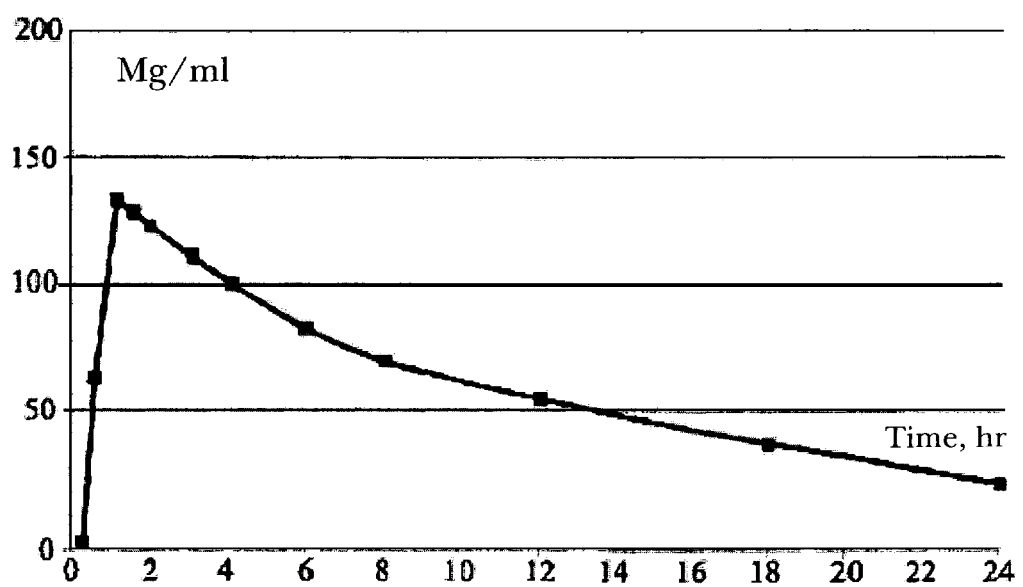

AGENT FOR INDUCING ENDOGENOUS INTERFERON

TECHNICAL FIELD

The invention relates to medicine and can be used for treating a range of diseases in the treatment of which interferon is used.

BACKGROUND ART

The diseases that are treated using interferon or inducers of its endogenous synthesis include the majority of virus infections, including herpetic infection, viral hepatitis A, B, C and certain tumors: larynx papilloma, metrofibroma, mastadenoma, pituitary adenoma etc., see RU 2105566 C1.

Certain medicinal drugs are known to induce the synthesis of own endogenous interferon—a substance that promotes the creation of a protective barrier that prevents infection of the organism by viruses and the growth of malignant cells. The most well-known and widespread interferon-inducing drugs are Neovir, Cycloferon that has the same structure, and Tilorone Neovir (oxodihydroacridinylacetate sodium), which was taken as a prototype of the present invention, is widely used for treating viral and bacterial infections, especially those caused by intracellular parasites. Neovir is also used in treatment of certain oncological diseases. Neovir has certain activity when administered by way of injection. When administered orally, this preparation has low effectiveness.

After ingestion of Neovir the maximal production of interferon is identified in the sequence of intestines-liver-blood after 4-24 h. Neovir induces the production of interferon in human leukocytes, and the level of interferon in blood amounts to 250 U/ml.

When prescribing Neovir, as well as other known inducers of interferon, there is a risk of undesirable reactions with other drugs, e.g. with Rifameipin when treating tuberculosis, and with antiretroviral drugs when treating HIV infection, as well as with oral contraceptives. Due to lack of detailed data on the interaction of Neovir with the abovementioned and certain other drugs, their simultaneous administration may be dangerous. Renton K W, Mannering G J (1976). "Depression of hepatic cytochrome P-450-dependent monooxygenase systems with administered interferon inducing agents". Biochem Biophys Res Commun. 73 (2): 343-343. DOI:http://dx.doi.org/10.1016/0006-291X(76)90713-0. PMID 187194).

SUMMARY OF THE INVENTION

It is an object oi the present invention to provide a preparation that exhibits greater activity both when injected and when administered orally.

According to the invention the agent for inducing endogenous interferon is comprised of the compound 6-(3-methoxycarbonyl phenyl) amino-2,4 (1H, 3H)-pyrimidinedione $C_{12}H_{11}N_3O_4$ of general formula:

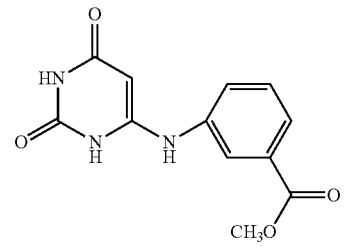

The applicant has not found any sources of information containing data on technical solutions identical to the present invention, which enables to conclude that the invention conforms to the criterion "Novelty" (N).

The applicant has not found any sources of information containing data on the influence of the features of the invention on the technical result produced by the invention, which consists in a considerable increase of inducing activity in various methods of administration, together with considerable reduction of adverse effects and undesirable reactions with other preparations. In applicant's opinion, this enables to conclude that the present technical solution conforms to the criterion "Inventive Step" (IS).

BRIEF DESCRIPTION OF THE DRAWINGS

The invention is further explained, by way of example, with reference to the drawing that shows the diagram of concentration of the substance in blood plasma oi rabbits during vagina) administration in the form of "vaginal suppositories 0.1 g".

PREFERRED EMBODIMENT

The inventive substance is produced as follows. 7 g of 6-aminouracil are added to 10 g of hydrochloride of methyl ether of m-aminobenzoic acid and 8.4 g of methyl ether of m-aminobenzoic acid, and then the mixture is thoroughly ground in a mortar. When heated to 160° C., the mixture is melted and becomes thinly fluid, but after just 0.5 h it becomes solidified, and the heating is discontinued after 1.5 h. The mixture is transferred to water, stirred and filtered, and washed with water. Then the product is boiled in 100 ml of ethyl alcohol for 2 h. After the mixture is cooled down to room temperature, the product is filtered, washed with ethyl alcohol and dried. 10 g of target product are obtained.

This product is the mixture of the inventive substance (monomer) with its dimer. The melting temperature of the mixture is above 300° C.

Separation of the monomer and the dimer was done as follows: the abovementioned target product was dissolved in a mixture of 2-propanol-dimethylformamide while heating, and then cooled down. During the cooling the dimer precipitated, and the monomer remained in the solution. In order to extract the monomer, the solution was stripped to dryness, and the crystal precipitate was washed with ethanol and dried in vacuum. The mass of the obtained monomer was twice the mass of the dimer; it is possible to use both the monomer and the dimer: that said, the dimer penetrates the cell membranes more easily.

Infrared spectrum of the preparation measured for pills with potassium bromide (2 mg per 300 mg of potassium bromide), in the region from 4000 cm$^{-1}$ to 400 cm$^{-1}$ must have complete matching of the absorption bands with the absorption bands of the attached spectrum in terms of positioning and relative intensity of the bands.

Ultraviolet spectrum of 0.025% solution of the preparation in 0.1 H solution of caustic soda in the region from 200 to 370 nm has the shoulder at 252 nm. absorption minimum at 265 nm and non-symmetric absorption maximum at 288 nm±1 nm.

Spectrum of proton magnetic resonance contains the following characteristic signals, ppm: 10.4 and 10.2 (NH endocycl.), 8.36 (exocycl. NH). 7.4-7.8 (4H, Ar.), 4.72 (1 H, CH), 3.86 (3 H, OCH$_3$).

The specified spectra are virtually identical for the inventive compound and its dimer.

When manufacturing pharmacological preparations on the basis of the inventive substance, various pharmacologically acceptable fillers, adjuvants and transporters can be used: methylcellulose, oxypropylmethylcellulose, carboxymethylcellulose, sodium carboxymethylcellulose, corn starch, talcum, kaolin, bentonites, aerosil, beet sugar, milk sugar, sodium chloride, sodium hydrocarbonate, aluminum oxide, aluminum stearate, lecithin, serum proteins, phosphates, glycine, sorbic acid, potassium sorbate, mixture of glycerides of saturated vegetable fatty acids, salts of zinc, colloid silicon dioxide, trisilicate of magnesium, wax, polyethyleneglycol, lanoline etc.

The inventive substance can be used orally, parenterally, through rectum, nasally, lingually, vaginally or by means of implants; parenteral administration in this case includes administration subdermally, intradermally, intravenously, intramuscularly, intraarticularly, intrasynovially, intrasternally, into cerebrospinal fluid, intracranially.

Topical application of pharmacological preparations created on the basis of the invention is especially recommended if the treatment is needed for areas of the organism that allow local application of the preparations.

In pharmacological preparations intended for topical skin application, the active substance should be combined with suitable ointment base that can contain the active substance in dissolved form or as a suspension. Said ointment base can include mineral oils, liquid petrolatum, white petrolatum, propylene glycol, a mixture of polyoxyethylene and polyoxypropylene, emulsifying wax and water. Pharmacological preparations intended for external use can also be based on a lotion or cream, which contains the inventive substance in the form of a solution or suspension. In this case fillers can be embodied as a mineral oil, sorbitan monostearate, Polysorbate 60, cetyl ethers, wax, cetearyl alcohol, 2-octyldodecanol, benzyl alcohol, water and other suitable ingredients. Pharmacological preparations based on the inventive substance can also be used for lower bowel segments in the form of rectal suppositories or any other suitable form of medicine.

The inventive substance can also be used for manufacturing such medical products for external use as plasters, nasal sprays or inhalers. Liquid phase for dissolving the inventive substance can be embodied as isotonic solution of sodium chloride (physiological solution); stabilizer can be embodied as benzyl alcohol or any other suitable substance; absorption activator can be embodied as fluorocarbons in order to increase the bioavailability; dissolution and dispersion can be improved by using any known auxiliary substances used in manufacture of such pharmacological products.

Medical preparation manufactured on the basis of the inventive substance can be used in the following dosages: approximately from 0.01 to 25 mg of the active substance per 1 kg of patient weight per 24 hours. For preventing and treating viral and bacterial infections, as well as certain forms of cancer, a preferable daily dosage is approximately from 0.5 to 25 mg of the active substance per 1 kg of weight. Pharmacological preparations on the basis of the invention can be administered from 1 to 5 times per day or in the form of a long-lasting infusion.

Determining the level of induced interferon (IFN) after administering the inventive substance.

Quantitative evaluation of IFN contents in the reference and experimental samples was performed according to two methods:

1) Using immunoenzymometric IFN test system ProCon IF2 plus manufactured by company "Proteinovyl kontur", with conversion of the obtained results of weight content of the IFN into international units (IU) of IFN activity.

2) Using an original technique of biological testing for IFN content, which consists in the following: IFN slows down the development of cytopathic effect of viruses, which manifests in the destruction of monolayer of a specially selected cell culture line. Quantitative determination of the IFN content in the sample is done by means of quantitative analysis of the intensity of destruction of the cellular monolayer after preincubation with IFN-containing samples and incubation with the indicator virus.

Brief description of the technique: a monolayer culture of cells of human lung carcinoma L-41 is incubated with titrated IFN-containing samples in microplates for 24 hours in a $CO_2$-thermostat at 37° C. after which a solution of the indicator virus is introduced into the microplates (a virus of vesicular stomatitis, strain of Indiana, VSV), and then incubation is performed for 18 hours in a $CO_2$-thermostat at 37° C. Then the microplates are stained by means of crystal violet in order to visualize the results. The surpluses of the stain are washed with distilled water, the microplates are dried, then the stain that contacted with the live cells is extracted by means of 30% ethanol, and the microplates are photometered at an automatic photometer like "Multiscan" for 96-well microplates in the mode of multiple well scanning at wave length of 590 nm. The obtained quantity of contacted stain is directly proportional to the IFN content in the tested sample. The quantitative contents of IFN in the samples are determined utter interpolating the results within the limits of dependency on the contents of IFN in the samples and the intensity of destruction of the cellular monolayer. This dependency is determined after performing titration in similar conditions for a standard reference preparation of native human IFN. A preparation of native human IFN standardized against activity was used as a reference preparation in each experiment. The results of the analysis are expressed in IU of IFN activity per ml in this induction system that contains 3-106 lymphocytes/ml. Experimental and reference points were examined in 4 parallels.

Interferon inducing activity of the preparations in vivo during intragastric administration to mice is shown in Table 1.

Data of Table 1 show that the inventive substance induces an increase of the level of endogenous interferon with dynamics that differs from that of the preparation used for comparison. The level of endogenous interferon after administration of the inventive substances exceeds that of the prototype.

Interferon inducing activity of the preparations in vivo during oral administration to mice is shown in Table 2.

Data of Table 2 show that the inventive substance, when administered orally, causes the production of endogenous interferon and is much more effective than the prototype.

Concentration in blood plasma of the experimental animals during vaginal administration of the inventive substance.

The results of measuring the concentration of the substance in blood plasma of rabbits during vaginal administration in the form of "vaginal suppositories 0.1 g" are shown on the provided diagram in the form of averaged pharmacokinetic curves (see FIG. 1). After inserting the suppository, the substance began to enter the general blood circulation after approximately 15 minutes; after 1 hour the concentration of the substance in the blood reached its maximum (approximately 120 μg/ml); then it was gradually excreted from the organism, and 24 hours after its administration the detected presence of the substance in blood plasma was minimal (approximately 20 μg/ml). The dispersion of individual values was moderate: coefficient of variation CV amounted to 13-22%.

The results of the conducted studies show that the inventive substance, when administered vaginally in the form of suppositories, enters the blood of the experimental animals.

Thus, it has been ascertained that the inventive substance has interferon-inducing activity in various methods of administration, and the activity of the inventive substance exceeds that of the prototype (Neovir) both during parenteral and oral administration. Also a significant reduction of adverse effects and undesirable reactions with other drugs has been noted.

INDUSTRIAL APPLICABILITY

The invention can be implemented by means of known materials and equipment. In applicant's opinion, this enables to conclude that the invention conforms to the criterion "Industrial Applicability" (IA).

Interferon Inducing Activity of the Preparations In Vivo During Intragastric Administration to Mice (in IU)

TABLE 1

| Preparation | Time | | | | |
|---|---|---|---|---|---|
| | 2 hours | 4 hours | 6 hours | 8 hours | 24 hours |
| Placebo | 7-10* | 20-25 | 7-10 | 7-10 | 7-10 |
| Neovir | 7-10 | 100-110 | 7-10 | 7-10 | 7-10 |
| The inventive substance, monomer | 30 | 10 | 160 | 25-30 | 30 |
| The same, dimer | 40 | 50 | 210 | 30-35 | 15-40 |

The preparations were administered in the amount 1000 μg/mouse
*Background value of interferon activity - 7-10 units.

Interferon Inducing Activity of the Preparations In Vivo During Oral Administration to Mice (in IU)

TABLE 2

| Preparation | Time | | | | |
|---|---|---|---|---|---|
| | 2 hours | 4 hours | 6 hours | 8 hours | 24 hours |
| Placebo | — | 20-25 | — | — | — |
| Neovir | 7-10 | 40-60 | 10-12 | 7-10 | 7-10 |
| The inventive substance, monomer | 18 | 120 | 20 | 40 | 100 |
| The same, dimer | 12-25 | 150 | 30 | 30-50 | 120 |

The preparations were administered in the amount 5.0 mg/mouse
*Background value of interferon activity - 7-10 units.

The invention claimed is:

1. A method of treating a viral infection in a patient in need thereof, said method comprising administering to said patient a composition comprising a therapeutically effective amount of an isolated dimer of a compound of the formula:

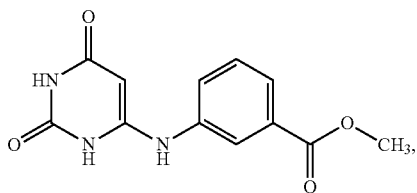 [SMILES: COC(=O)c1cccc(Nc2cc(=O)[nH]c(=O)[nH]2)c1]

wherein said viral infection is selected from the group consisting of: herpetic infections; HIV; influenza virus; papillomavirus; and viral hepatitis A, B, C or E.

2. The method of claim 1, wherein said composition further comprises at least one pharmacologically acceptable filler, adjuvant or transporter selected from the group consisting of: methylcellulose, oxypropylmethylcellulose, carboxymethylcellulose, sodium carboxymethylcellulose, corn starch, talcum, kaolin, bentonites, aerosil, beet sugar, milk sugar, sodium chloride, sodium hydrocarbonate, aluminum oxide, aluminum stearate, lecithin, serum proteins, phosphates, glycine, sorbic acid, potassium sorbate, mixture of glycerides of saturated vegetable fatty acids, salts of zinc, colloid silicon dioxide, trisilicate of magnesium, wax, polyethyleneglycol, and lanoline.

3. The method of claim 1, wherein the composition is administered vaginally.

4. The method of claim 1, wherein the composition is administered at a compound dosage of from about 0.01 mg/kg/day to about 25 mg/kg/day.

5. The method of claim 4, wherein the composition is administered at a compound dosage of from about 0.5 mg/kg/day to about 25 mg/kg/day.

6. The method of claim 1, wherein the composition is administered at a compound dosage of about 0.1 g per day.

7. The method of claim 1, wherein the composition is in a form of a suppository.

8. The method of claim 1, wherein said isolated dimer is produced by a method comprising the steps of:
  (a) combining 6-aminouracil, hydrochloride of methyl ether of m-aminobenzoic acid, and methyl ether of m-aminobenzoic acid;
  (b) heating the combination of step (a) until solidified;
  (c) solvating the solid produced in step (b) in water;
  (d) filtering the solvated solid produced in step (c);
  (e) boiling the filtrate produced in step (d) in ethyl alcohol;
  (f) cooling the boiled filtrate produced in step (e) to room temperature and washing the filtrate with ethyl alcohol;
  (g) drying the filtrate produced in step (f);
  (h) dissolving the dried filtrate of step (g) in 2-propanol-dimethylformamide while heating;
  (i) cooling the solution of step (h) until a precipitate is formed; and isolating the precipitate of step (i).

9. A method of treating a tumor in a patient in need thereof, said method comprising administering to said patient a composition comprising a therapeutically effective amount of an isolated dimer of a compound of the formula:

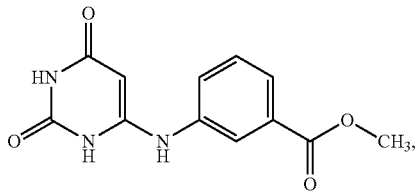 [SMILES: COC(=O)c1cccc(Nc2cc(=O)[nH]c(=O)[nH]2)c1]

wherein said tumor is selected from the group consisting of: larynx papilloma; metrofibroma; mastadenoma; endometrial carcinoma; and pituitary adenoma.

10. The method of claim 9, wherein said composition further comprises at least one pharmacologically acceptable filler, adjuvantor transporter selected from the group consisting of: methylcellulose, oxypropylmethylcellulose, carboxymethylcellulose, sodium carboxymethylcellulose, corn starch, talcum, kaolin, bentonites, aerosil, beet sugar, milk sugar, sodium chloride, sodium hydrocarbonate, aluminum oxide, aluminum stearate, lecithin, serum proteins, phosphates, glycine, sorbic acid, potassium sorbate, mixture of glycerides of saturated vegetable fatty acids, salts of zinc, colloid silicon dioxide, trisilicate of magnesium, wax, polyethyleneglycol, and lanoline.

11. The method of claim 9, wherein the composition is administered vaginally.

12. The method of claim 9, wherein the composition is administered at a compound dosage of from about 0.01 mg/kg/day to about 25 mg/kg/day.

13. The method of claim 12, wherein the composition is administered at a compound dosage of from about 0.5 mg/kg/day to about 25 mg/kg/day.

14. The method of claim 9, wherein the composition is administered at a compound dosage of about 0.1 g per day.

15. The method of claim 9, wherein the composition is in a form of a suppository.

16. The method of claim 11, wherein the composition is in a form of a suppository.

17. The method of claim 9, wherein said isolated dimer is produced by a method comprising the steps of:
(a) combining 6-aminouracil, hydrochloride of methyl ether of m-aminobenzoic acid, and methyl ether of m-aminobenzoic acid;
(b) heating the combination of step (a) until solidified;
(c) solvating the solid produced in step (b) in water;
(d) filtering the solvated solid produced in step (c);
(e) boiling the filtrate produced in step (d) in ethyl alcohol;
(f) cooling the boiled filtrate produced in step (e) to room temperature and washing the filtrate with ethyl alcohol;
(g) drying the filtrate produced in step (f);
(h) dissolving the dried filtrate of step (g) in 2-propanol-dimethylformamide while heating;
(i) cooling the solution of step (h) until a precipitate is formed; and isolating the precipitate of step (i).

18. A method of treating a bacterial infection in a patient in need thereof, said method comprising administering to said patient a composition comprising a therapeutically effective amount of an isolated dimer of a compound of the formula:

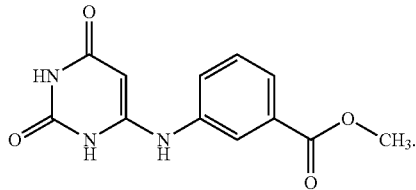 [SMILES: COC(=O)c1cccc(Nc2cc(=O)[nH]c(=O)[nH]2)c1]

19. The method of claim 18, wherein said composition further comprises at least one pharmacologically acceptable filler, adjuvant or transporter selected from the group consisting of: methylcellulose, oxypropylmethylcellulose, carboxymethylcellulose, sodium carboxymethylcellulose, corn starch, talcum, kaolin, bentonites, aerosil, beet sugar, milk sugar, sodium chloride, sodium hydrocarbonate, aluminum oxide, aluminum stearate, lecithin, serum proteins, phosphates, glycine, sorbic acid, potassium sorbate, mixture of glycerides of saturated vegetable fatty acids, salts of zinc, colloid silicon dioxide, trisilicate of magnesium, wax, polyethyleneglycol, and lanoline.

20. The method of claim 18, wherein the composition is administered vaginally.

21. The method of claim 18, wherein the composition is administered at a compound dosage of from about 0.01 mg/kg/day to about 25 mg/kg/day.

22. The method of claim 21, wherein the composition is administered at a compound dosage of from about 0.5 mg/kg/day to about 25 mg/kg/day.

23. The method of claim 18, wherein the composition is administered at a compound dosage of about 0.1 g per day.

24. The method of claim 18, wherein the composition is in a form of a suppository.

25. The method of claim 20, wherein the composition is in a form of a suppository.

26. The method of claim 18, wherein said isolated dimer is produced by a method comprising the steps of:
(a) combining 6-aminouracil, hydrochloride of methyl ether of m-aminobenzoic acid, and methyl ether of m-aminobenzoic acid;
(b) heating the combination of step (a) until solidified;
(c) solvating the solid produced in step (b) in water;
(d) filtering the solvated solid produced in step (c);
(e) boiling the filtrate produced in step (d) in ethyl alcohol;
(f) cooling the boiled filtrate produced in step (e) to room temperature and washing the filtrate with ethyl alcohol;
(g) drying the filtrate produced in step (f);
(h) dissolving the dried filtrate of step (g) in 2-propanol-dimethylformamide while heating;
(i) cooling the solution of step (h) until a precipitate is formed; and isolating the precipitate of step (i).

27. An isolated dimer of a compound of the formula:

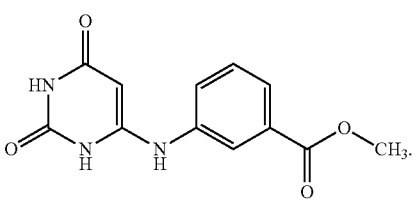 [SMILES: COC(=O)c1cccc(Nc2cc(=O)[nH]c(=O)[nH]2)c1]

* * * * *